April 4, 1944. V. C. KONDO Plant Pat. 622
GARDENIA PLANT
Filed Sept. 13, 1943
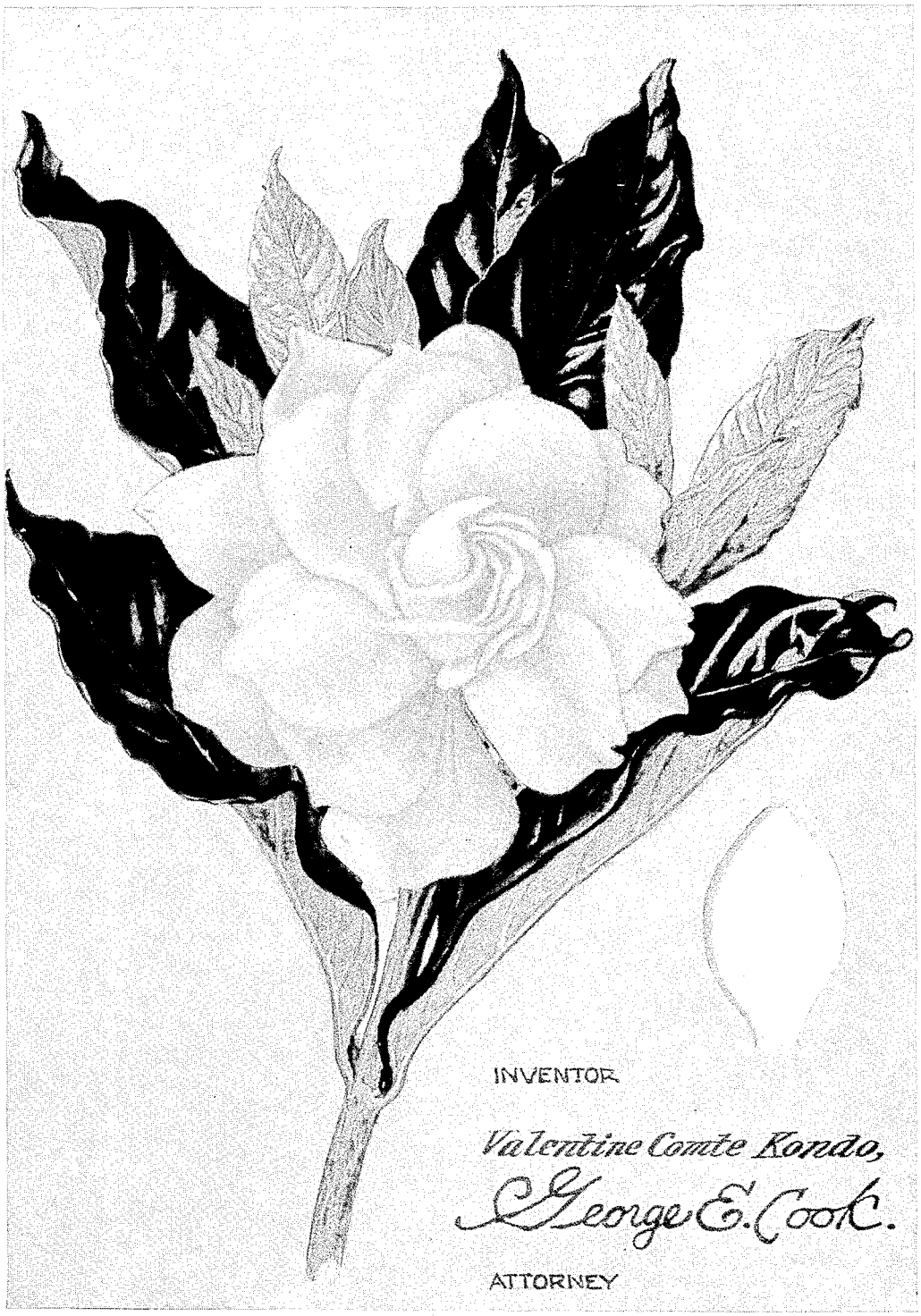

Patented Apr. 4, 1944

Plant Pat. 622

UNITED STATES PATENT OFFICE

622

GARDENIA PLANT

Valentine Comte Kondo, Miami, Fla.

Application September 13, 1943, Serial No. 502,208

1 Claim. (Cl. 47—60)

My present discovery relates to improvement in gardenia plants. My new variety is a sport of the variety Veitchii and was developed and improved by selection for a number of years. The plant shows some of the distinctive characteristics of its parent although it is very different in many respects.

Probably most outstanding among the many good qualities of this new variety is the fact that the flowers can be handled roughly without bruising, whereas most gardenias turn brown at the slightest touch. This quality enables my new variety to be shipped easily and still remain fresh and beautiful for many days after being received. Its large size is also very notable, since it often attains a size of 5 to 6 inches in diameter, with two more rows of petals than other commercial gardenias. Its petals stay flat when the flower opens and produce the desirable and unusual camellia-like form. Its fragrance is sweet and overwhelming and distinctly of the magnolia type which is more pleasing than that of most gardenias.

The original illustration making a part of this specification shows a typical flower branch of my new variety, giving particular attention to the arrangement of the leaves; also the reverse side of a single first-row petal.

Following is a detailed description of the plant and flower of my new variety.

*The plant*

Growth: Vigorous and strong. Fastest growing plant among commercial gardenias. In 6 months it will attain a height of 2 to 3 feet.

Disease resistance: Free from disease, particularly leaf spot which is found among other varieties.

Blooming habits: Heavy producer. Blooms when most other varieties fail to bloom under similar conditions of growth. Buds do not drop at any season of the year, whereas most commercial gardenias have this fault. Each branch produces a single bud which is surrounded by a whorl of leaves. Blooming season of this variety in my nursery is from November to July.

Foliage: Very large, from 4 to 7½ inches long by 2 to 4 inches wide. Mature foliage is very dark green, almost black on the lower branches. Under surface and new foliage is lighter. Upper surface is glossy.

Stems: Brown on the hard wood (like Veitchii). Sturdy. Strong.

*The flower*

Bud: Three to four inches long; looks much like a large magnolia bud. *Peduncle* is about 2 inches long and very heavy. *Calyx* is 1½ to 2 inches long. *Sepals* are open.

Blossom:

*Size.*—Large; 4 to 6 inches in diameter.

*Form.*—Regular and camellia-like. Petals remain flat rather than become reflexed.

*Color.*—Pure waxy white like other gardenias, except that it has a ribbon of "cream green" around the under edge of each petal of the first row. When open, the flower shows no black center as gardenias frequently do.

*Petals.*—Very thick and substantial. They are rounded from the base, smooth, and velvety in aspect.

*Petallage.*—The flower averages more than 25 petals which require 7 to 10 days in which to open. This is two more rows of petals than are found in other commercial gardenias.

*Fragrance.*—Very sweet and distinctly of the magnolia type.

*Endurance.*—Unlike other known gardenias, this variety can be handled roughly without bruising and turning brown.

*Lasting period.*—When on the plant, the flower remains white from 6 to 10 days, after which it turns a pure cream color and remains beautiful for several days longer. When cut, it keeps from 10 days to 2 weeks.

Having thus disclosed my discovery, I claim:

The new and useful variety of gardenia plant, substantially as herein shown and described, characterized particularly by its vigorous, fast growth; its freedom from disease; its constant heavy production of flowers; the retention of its buds at all seasons; its production of a single bud to a branch; its large, dark, glossy foliage which forms in a whorl; its large buds of magnolia-like appearance; its very large, camellia-like flowers with great petallage and with substantial, rounded petals of pure white with greenish cream edging on under side of outer row; the sweet magnolia-like fragrance of its flowers; and the great endurance and longevity of its flowers both on the bush and after being cut.

VALENTINE COMTE KONDO.